US006896871B2

(12) United States Patent
Karpeisky et al.

(10) Patent No.: US 6,896,871 B2
(45) Date of Patent: May 24, 2005

(54) BIPHOSPHONATE CONJUGATES AND METHODS OF MAKING AND USING THE SAME

(75) Inventors: Marat Karpeisky, deceased, late of Boulder, CO (US); by Alexander Karpeisky, legal representative, Lafayette, CO (US); Nelly Padioukova, Moscow (RU); Sergey Mikhailov, Moscow (RU); H.B.F. Dixon, Cambridge (GB); Grigorii Tzeitline, Moscow (RU)

(73) Assignee: MBC Research, Inc., Boulder, CO (US)

( * ) Notice: Subject to any disclaimer, the term of this patent is extended or adjusted under 35 U.S.C. 154(b) by 380 days.

(21) Appl. No.: 09/833,083

(22) Filed: Apr. 10, 2001

(65) Prior Publication Data

US 2002/0142994 A1 Oct. 3, 2002

Related U.S. Application Data

(63) Continuation-in-part of application No. 09/731,598, filed on Dec. 7, 2000, which is a continuation-in-part of application No. 09/283,440, filed on Apr. 1, 1999, now Pat. No. 6,214,812.
(60) Provisional application No. 60/080,500, filed on Apr. 2, 1998.

(51) Int. Cl.$^7$ .......................... A61K 51/00; C07F 51/00; C07F 9/00; C07F 13/00
(52) U.S. Cl. .................... 424/1.77; 424/1.11; 424/1.65; 424/9.1; 534/10; 534/14; 514/89; 514/107; 514/108; 546/22; 546/24
(58) Field of Search ....................... 546/22, 24; 514/89, 514/107, 108; 424/1.77, 1.11, 1.65, 9.1; 534/10, 14

(56) References Cited

U.S. PATENT DOCUMENTS

| | | | |
|---|---|---|---|
| 4,621,077 A | 11/1986 | Rosini | 514/108 |
| 5,130,304 A | 7/1992 | Binderup | 514/91 |
| 5,358,941 A | 10/1994 | Bechard | 514/102 |
| 5,488,041 A | 1/1996 | Barbier | 514/108 |
| 6,121,253 A | 9/2000 | Han et al. | 514/102 |
| 6,140,518 A | 10/2000 | Gallagher et al. | 552/506 |

FOREIGN PATENT DOCUMENTS

| | | |
|---|---|---|
| WO | 88/00829 | 2/1988 |
| WO | 91/10646 | 7/1991 |
| WO | WO 98/35704 | 8/1998 |

OTHER PUBLICATIONS

Hosain et al., "Targeted Delivery of Antineoplastic Agent to Bone: Biodistribution Studies of Technetium–99m–Labeled–Gem–Biphosphonate Conjugate of Methotrexate", The Journal of Nuclear Medicine, vol. 37, No. 1, Jan. 1996.

Reinholz et al., "Distinct Mechanisms of Bisphosphonate Action Between Osteoblasts and Breast Cancer Cells: Identity of a Potent New Biophosphonate Analoque", Breast Cancer Research and Treatment 71: 257–268, 2002.

Fleisch, *Endocrine Reviews*, 19(1), pp. 80–100 (1998).

Klein, *Journal of Cellular Biochemistry*, 68, pp. 186–194 (1998).

Rogers et al., *Molecular Pharmacology*, 47, pp. 398–402 (1995).

*Primary Examiner*—Evelyn Mei Huang
(74) *Attorney, Agent, or Firm*—Sheridan Ross P.C.

(57) ABSTRACT

The present invention is directed to particular bisphosphonate compounds, and in particular, to bisphosphonate conjugates that are useful in the treatment of soft tissues surrounding bone and bone-related diseases, such as bone cancer and osteoporosis.

11 Claims, 3 Drawing Sheets

Reagents & Conditions: i) EtOH/water; ii) NaBH$_4$/EtOH/water a: R=H
b: R=PO$_3$H$_2$

BIPHOSPHONATE CONJUGATES AND METHODS OF MAKING AND USING THE SAME

RELATED APPLICATIONS

This application claims priority from U.S. Provisional Patent Application No. 60/080,500 filed Apr. 2, 1998 and is a continuation-in-part application of U.S. patent application Ser. No. 09/283,440 filed on Apr. 1, 1999 U.S. Pat. No. 6,214,812 and U.S. patent application Ser. No. 09/731,598 filed on Dec. 7, 2000. The entire disclosure of these applications is considered to be part of the disclosure of the accompanying application and is hereby incorporated by reference.

FIELD OF THE INVENTION

The present invention is directed to particular bisphosphonate compounds, and in particular, to bisphosphonate conjugates that are useful in the treatment of soft tissues surrounding bone and bone-related diseases, such as bone cancer and osteoporosis.

BACKGROUND OF THE INVENTION

Bisphosphonates are known to be useful in the treatment of degenerative bone disorders. Bone degeneration diseases, including Paget's Disease and osteoporosis, have proven difficult to treat because the mechanisms involved are not well understood. Bisphosphonic acid derivatives are known to be osteoselectively taken up by bone tissue. Moreover, bone scanning agents based on the use of some bisphosphonic acid compounds have been used in the past to achieve desirable high definition bone scans (see e.g., U.S. Pat. No. 4,810,486 to Kelly et. al). Other bisphosphonate derivatives have been used as therapeutic agents for bone diseases such as osteoporosis, rheumatoid arthritis, and osteoarthritis (see e.g., U.S. Pat. No. 5,428,181 to Sugioka et. al). Finally, bisphosphonate compounds are known as being useful in inhibiting bone loss, believed to act in a manner which hinders the activity of osteoclasts, so that bone loss is diminished. Bisphosphonate therapy has, however, in the past, frequently been accompanied by severe side effects, such as severe adverse effects on bone development and overall somatic growth.

A need exists for compounds which have the ability to inhibit bone resorption effects and that inhibit mineralization without an increase in toxicity. Moreover, a need exists for compounds that may be useful to deliver bisphosphonates to a cell and within a cell. It is believed that by providing an ability to supply bisphosphonate to a cell, entry ports into the cell can be blocked, thus facilitating various treatment regimens. Alternatively, delivery of bisphosphonate to and within a cell by use of particular delivery agents, may facilitate incorporation into the cell of bisphosphonate compounds which then can be used by the cell in ameliorative ways. A need exists for novel bisphosphonate as a delivery vehicle that can selectively target bone and deliver therapeutic drugs or toxins to bone and surrounding soft tissue, leading to unique and novel treatment regimens. Finally, a need exits or improved bisphosphonate compounds that can aid in bone scanning diagnostics.

SUMMARY OF THE INVENTION

Although basic structural requirements for bisphosphonate actions have been defined, the precise structure-activity relations have not been defined, and thus, the molecular mechanisms of action are still unknown. Rational design of compounds for various clinical indications is therefore stymied without an appreciation of such molecular mechanisms. Moreover although many bisphosphonates have been synthesized, each of them has shown its own physicochemical and biologic characteristics, and thus, it is not possible to extrapolate from the results of one compound to others with respect to their actions (see e.g. Fleisch, "*Mechanisms of Action of the Bisphosphonates*" Medicina, Buenos Aires, 57:65–75 1997). The biological effects of bisphosphonates in calcium-related disorders are attributed to the incorporation of the bisphosphonates in bone, enabling direct interaction with osteoclasts and/or osteoblasts. The high accumulation of bisphosphonates in bone, due to their high affinity for hydroxyapatite (HAP), is essential for mediating in vitro and in vivo activity.

One aspect of the present invention relates to the synthesis, pharmaceutical composition and medical use of bone-seeking bioconjugates made up of natural vitamins and known bisphosphonates. Nitrogen-containing bisphosphonates are known to act by binding to a specific intracellular target at a site that is complementary in structure to the bisphosphonate side chain. In particular, vitamin B6 and its phosphorylated derivatives are known to have high affinity to different proteins, in addition they can enhance transport of small molecular weight compounds (in form of prodrug) through cell membrane. Thus, vitamin B6-bisphosphonate conjugates may have a dual role: (1) a new highly effective bone disease drug; and (2) a specific vehicle for delivery of known bisphosphonates to intracellular targets. In particular, pharmaceutically acceptable vitamin B6-bisphosphonate conjugates and their salts of the present invention are characterized in that they have the general structure:

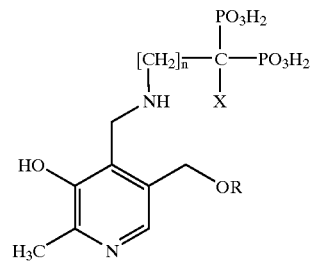

n = 0–6
R = H, $PO_3H_2$, $SO_3H$
X = H, OH, $NH_2$, $SR^2$, Alk, Ar, HetAr
$R^2$ = H, Alk, Ar, HetAr, $SR^2$

Vitamin B6-bisphosphonate Conjugates

The pharmaceutical compositions of the present invention, as described herein below, offer an attractive delivery vehicle in which to deliver and concentrate drugs and proteins to normal and abnormal bone tissue, soft tissue surrounding bone and bony lesions. Bony lesions include but are not limited to cancer, osteomyelitis, soft tissue infection surrounding bone, bone marrow, bone disease such as Paget's disease, etc.

In addition, such compositions may include bone-seeking radioisotope conjugates for use in imaging and therapy. In particular the use of technetium (Tc) and rhenium (Re) for imaging and therapy of bone is encompassed by the present invention. Preferably, the isotopes Tc99m, Re 184 and Re 186 are utilized for imaging (Tc) and for therapeutic applications (Re). Re184 and Re186 both emit high energy beta-particles. Re184 and Re186 can be obtained, for example, from NeoRx, Seattle, Wash., or other sources. Re 186 also emits a gamma ray that can be detected by a gamma camera.

Yet another aspect of the present invention relates to bisphosphonate conjugates that are capable of releasing antibacterial and cytotoxic components upon binding with bone tissue. Such conjugates are useful in the treatment and prevention of bone cancer and bone infections.

To find substances that are useful for the treatment of the primary bone tumors, as well as bone metastasis, the present inventors synthesized and tested novel bisphosphonate conjugates containing both an osteotropic and an antineoplastic (cytotoxic) moiety released upon binding of said conjugates to bone. The chemical bond(s) connecting bisphosphonate and the drug is both stable enough to survive in the bloodstream and yet is cleaved to liberate the drug when the conjugate binds to bone.

For example, in the case of osteomyelitis (bone infection), certain therapeutic antibiotics can be coupled to the bisphosphonate carrier molecule for delivery of high concentrations of antibiotic to various sites of bone infection. Examples of antibiotics include ciprofloxacin (a fluoroquinolone), ampicillin (a penicillin antibiotic), gentamycen (an aminoglycoside antibiotic) and cefalex (a cephalosporin antibiotic). The present invention thus provides certain novel bisphosphonate conjugates, pharmaceutical compositions, and methods of using such analogs in the treatment of bone cancer and other bone-related diseases. Examples of nucleoside derivatives useful in the present invention include 5-fluorouracil and inosine triphosphate derivatives. The biological activity of phosphonate conjugates and other molecules containing P—O—P—C—P type bonds, are demonstrated by both in vitro and in vivo models. The pharmaceutically acceptable salts and esters of the invention are characterized in that they have the general structure:

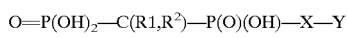

O=P(OH)$_2$—C(R1,R$^2$)—P(O)(OH)—X—Y where X=O$_1$S$_1$N atom, Y=residue of cytotoxic or antibiotic compound;
where R$^1$=H; R$^2$=OR$^3$, NR$^3$, SR$^3$, R$^3$ and
R$^3$=H, alkyl, aryl, cycloalkyl, heteroyl, NH$_2$.

Novel Bisphosphonate Conjugate-substituted Triphosphates

One aspect of the present invention is thus directed to the synthesis of pharmaceutical compositions and medical uses of such compositions. Particular embodiments of the present invention include anti-cancer drugs that are coupled to bisphosphonate, such drugs including but not limited to 5-fluorouracil, cisplatin, doxorubicin, methotrexate, antibiotics such as ciprofloxacine, aminoglycosides, penicillin, cephalosporins, quinolones, protein toxins, protein and/or peptide growth factors and/or hormones that promote bone growth and bone marrow proliferation. Yet a further aspect of the present invention relates to the synthesis of novel bisphosphonates, pharmaceutical compositions incorporating the same and medical uses for such compositions. Various formulations of the inventive compounds as set forth herein can be administered, for example orally, by the use of pills, capsules, vitamin compositions, over-the-counter health drinks, etc.

DETAILED DESCRIPTION OF THE PREFERRED EMBODIMENT

Figure 1:
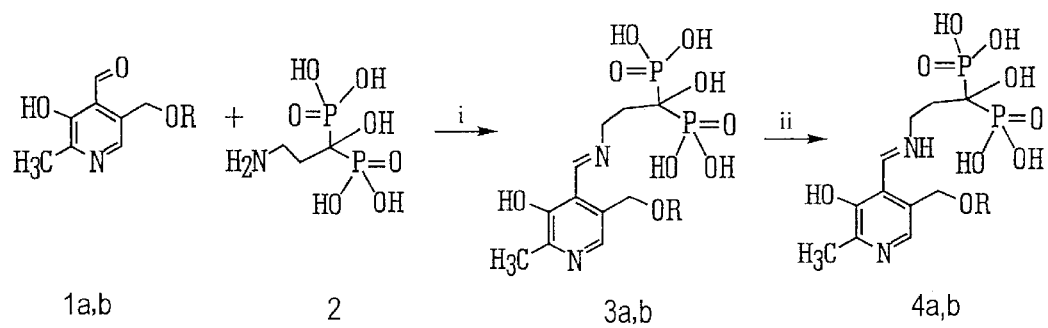
FIG. 1 is the scheme for the synthesis of vitamin B6-bisphosphonate conjugates.

Bisphosphonates-synthetic compounds containing two phosphonate groups bound to the central geminal atom are in widespread use to prevent bone resorption in a number of metabolic and tumor-induced bone diseases, including multiple myeloma. Recent reports suggest that bisphosphonate treatment may be associated with an increase in patient survival, indicating that these compounds have a direct effect on the tumor cells. Bisphosphonates contain two additional chains (R-1 and R-2, respectively) bound to a central geminal carbon. The availability of two side chains allows numerous substitutions and the development of a variety of analogs with different pharmacological properties. The activity varies greatly from compound to compound, the newest bisphosphonates being 5,000 to 10,000 times more active than etidronate, the first bisphosphonate described. The mechanism of action involves:

a) a direct effect on the osteoclast activity;

b) direct and indirect effects on the osteoclast recruitment, the latter mediated by cells of the osteoblastic lineage and involving the production of an inhibitor of osteoclastic recruitment; and c) a shortening of osteoclast survival by apoptosis. Large amounts of bisphosphonates can also inhibit mineralization through a physicochemical inhibition of crystal growth. The R-1 structure, together with the P—C—P are primarily responsible for binding to bone mineral and for the physicochemical actions of the bisphosphonates. A hydroxy group at R-1 provides optimal conditions for these actions. The R-2 is responsible for the antiresorptive action of the bisphosphonates and small modifications or conformational restrictions of this part of the molecule result in marked differences in antiresorptive potency. The presence of a nitrogen function in an alkyl chain or in a ring structure in R-2 greatly enhances the antiresorptive potency and specificity of bisphosphonates for bone resorption and most of the newer potent bisphosphonates contain a nitrogen in their structure.

Recent evidence suggests that the whole bisphosphonate molecule is essential for antiresorptive action. Thus, although the basic structural requirements for bisphosphonate actions have been defined, precise structure-activity relationships for the bisphosphonate side chains indicate that at least the newer generations of nitrogen-containing bisphosphonates act by binding to a specific target at a site that is complementary in structure to the bisphosphonate side chain. Vitamin B6 and its phosphorylated derivatives are known to have high affinity to different proteins. In addition they can enhance transport of small molecular weight compounds through cell membrane. The present invention is thus directed to the design and synthesis of novel vitamin B6-derivatives for use in the treatment and diagnosis of bone diseases. The novel B6-conjugates of the present invention are well suited for the treatment of disorders relating to the metabolism of calcium and of other, especially bivalent, metals. They may be used both for the treatment of diseases in the skeletal system, especially of bone formation and resorption disorders, such as of osteoporosis and Paget's disease, as well as for the treatment of diseases in the soft tissues, such as of deposition and mineralization conditions and bone formation.

The present invention also relates to bone-seeking complexes of technetium-99m, rhenium184, rhenium 186, and methods of preparing said complexes and compositions for use in the preparation of said complexes. In April 1971, G. Subramanian and J. O. McMee described (Radiology, 99, 192-a) bone scanning agent prepared by reducing pertechnetate TcO4-with stannous chloride in the presence of tripolyphosphate. The resulting labeled complex showed good skeletal uptake but suffered from several disadvantages, the most important of which was a 24-hour delay between injection and scanning (so that high levels of radioactivity were required in order to obtain adequate images), and the instability of the tripolyphosphate with respect to hydrolysis. An intensive search in the 1970's for better phosphate and phosphonate-based bone scanning agents has resulted in a large number of publications and several commercial products. The most widely used compound is methylenediphosphonate (MDP), the complex of which, with Tin and Technetium-99m, is the subject of U.S. Pat. No. 4,032,625. Recent introductions to the market have included hydroxymethylene diphosphonate (RDP), which is the subject of European Patent Application No. 7676; and 1,1-diphosphonopropane-2,3-dicarboxylic acid (DPD), which described in German O.S.No. 2755874.

A successful bone scanning agent and bone therapy requires high and rapid uptake of the agent in bone with clearance from the blood and soft tissues, such as muscle, of that part of the agent not taken up in the bone. In order to achieve scans of high definition, current bone agents normally require an interval of two hours or even more between injection of the agent into the patient and performance of the scan (the word "scan" is here taken to include gamma-camera imaging techniques, etc.). Even small reductions of the interval between injection and scanning are highly desirable and lead to worthwhile increases in convenience to the patient and the physician and in the efficiency in the running of nuclear medicine units. One aspect of the present invention arises from the novel discovery that some new bone-scanning agents, using Tc99m and bone therapy agents using Re 184 or Re 186, based on the use of a geminal bisphosphonate, can be coupled to compounds of vitamin B6-group and their phosphorylated derivatives. Thus, one aspect of the present invention is to provide a composition for use in the preparation of a bone-scanning agent comprises a mixture of a B6-conjugate (such as that disclosed herein), or a non-toxic salt, the pertechnetate, or rhenate, together with a reducing agent for pertechnetate or rhenate ions.

Preferred B6-conjugates include but are not limited to:
3-(N-pyridoxylamino)-1-hydroxy-propyliden-1,1-bisphosphonic acid and
3-(N-[5'-phospho]-pyridoxyl amino)-1-hydroxy-propyliden-1,1-bisphosphonic acid.
Preferably, the B6-conjugates used in the present invention contain at least one pyridoxamine residue. Representative compounds include the following:
(i) 3-(N-[5'-phospho]-pyridoxylamino)-1-hydroxypropyliden-1,1-bisphosphonic acid;
(ii) 3-(N-pyridoxylamino)-1-hydroxypropyliden-1,1-bisphosphonic acid;
(iii) 1-(N-[5'-phospho]-pyridoxylamino)-methylene-1,1-bisphosphonic acid;
(iv) 1-(N-pyridoxyl amino)-methylen-1,1-bisphosphonic acid;

The preferred complexing agent of the invention is 3-(N-pyridoxylamino)-1-hydroxy-propyliden-1,1-bisphosphonic acid, which shows high and rapid uptake in bone without any apparent concomitant disadvantages. 3-(N-pyridoxylamino)-1-hydroxypropyliden-1,1-bisphosphonic acid, is believed to be a new compound and, accordingly, this compound and its derivatives (e.g., its various salts, including sodium salts) forms a further aspect of the invention. This compound, as its sodium salt, may be prepared according to the reaction scheme shown on FIG. 1.

The bone-scanning agent or bone therapy agent of the present invention may be prepared by mixing an aqueous solution of the B6-conjugate complexant, or a non-toxic salt thereof, with a solution of the reducing agent. The pH of the mixture may, if desired, be adjusted within the range of from about 3 to about 9, preferably between about 4 to about 8. If desired, the mixture may be dispersed into sealed vials, freeze dried and, if not already sterile, finally sterilized.

Known reducing agents for pertechnetate and rhenate include tin (2+), iron (2+) and chromium (2+) salts, as well as metallic tin. More particularly, a stannous salt can be used as a reducing agent for this purpose and is preferred in the present invention. When the reducing agent is a stannous salt, the use of a stabilizer, or the nontoxic salt, in a molar excess over the salt, helps stabilize the composition. When stannous chloride is used as the reducing agent, it may be used in the preparation of the composition as an ethanolic solution in order to minimize problems due to hydrolysis. The composition may also include an inert agent to aid in dispersing small amounts of the composition into individual vials. In addition, other known additives may be included in the compositions, such as the stabilizing agent's nitrate, nitrite or para-aminobenzoate acid. A preferred formulation of the composition of the invention will contain from about 0.1 to about 1.0 mg stannous chloride with from about 1 to about 50 micrograms of technetium or the sodium salt thereof, in a vial for activation by from about 1 to about 15 ml of saline eluate from a technetium-99m or rhenium 184 or rhenium 186 generator.

The synthesis of preferred B6-conjugates was carried out according to Scheme 1, which is incorporated herein in its entirety.

Another aspect of the present invention relates to bisphosphonate conjugates that are capable of releasing antibacterial and cytotoxic components upon binding with bone tissue. Such conjugates are useful in the treatment and prevention of bone cancer and bone infections.

Novel nucleotide-bisphosphonate conjugates, molecules containing P—O—P—C—P type bonds, can be considered as derivatives and analogs of nucleoside 5'-triphosphates. For this reason, known methods for synthesis of nucleoside 5'-triphosphates were tested to work out effective experimental protocols for synthesis and purification of novel nucleotide-bisphosphonate conjugates. A variety of chemical methods for the preparation of nucleoside 5'-triphosphates from nucleoside monophosphates are known. We have chosen to activate the nucleoside monophosphates as imidazolides, using the 1,1'-carbonyldiimidazole method because the reaction of mononucleotides with 1,1'-carbonyldiimidazole (CDI) occurs under relatively mild conditions compared with other methods and does not require a purification step. For example, reaction of tri-n-butylammonium salt of 5'-IMP with CDI, followed by addition of tri-n-butylammonium salt of methylenediphosphonic acid in dry DMF, gave corresponding triphosphate (I) in a high yield (74%). In the same manner triphosphates II–III (FIG. 2) were obtained starting from nucleoside 5'-monophosphates. The separation of products were achieved on a column chromatography on DEAE-cellulose in bicarbonate form using concentration gradient of ammonium bicarbonate solutions. The yields are summarized in the Examples below. The structures of prepared derivatives were proved by $^1$H and $^{31}$P NMR spectra (see Examples). $^1$H NMR spectra of triphosphates I–III (FIG. 2) are near the same as for corresponding analogs of nucleoside 5'-monophosphates. The chemical shifts of phosphorus signals in $^{31}$P NMR spectra of the obtained derivatives I–III (FIG. 2) are similar to the earlier published for pCH$_2$ppA.

Analogous condensation of nucleoside imidazolides with 1-hydroxyethyliden-1,1-bisphosphonic acid gave the corresponding triphosphates in poor yield due to the instability of modified triphosphate residue during product isolation. Much better yields were obtained when the product separation was carried out under slightly acidic conditions, using column chromatography on DEAE-cellulose in CH$_3$COO$^-$ form in gradient concentration of lithium acetate (pH 4.6). It is known that the reaction of nucleoside 5'-monophosphates with CDI gave 2',3'-O-cyclic carbonates, which were very sensitive to alkaline treatment.

In the case of the preparation of analogs (VI, VII, IX, FIG. 2) the corresponding 2',3'-O-cyclic carbonates were obtained in good yield.

Following the recommendations of A. Hampton we used mild treatment with 0.5% aqueous triethylamine at room temperature for 0.5 h. The isolation of the desired derivatives (V, VII, IX) was achieved using HPLC. Due to the lower solubility of cytosine derivatives in dry DMF we have used in the case of preparation of VIII and IX, tri-n-octylammonium salts of nucleotide-5'-phosphates. A purity of derivatives thus obtained was checked by HPLC and their structure was confirmed by $^1$H and $^{31}$P $^1$H-NMR spectra. In PMR spectra of compounds IV–IX (FIG. 2) the signal of methyl group P—C(—Me)—P appeared around 1.5 ppm as a triplet. Three signals of phosphorus were found in $^{31}$P NMR spectra. The location of chemical shifts and the observed coupling constants Jp$_\alpha$p$_\beta$; J=30–33 Hz and Jp$_\gamma$p$_\beta$= 33–39 Hz were in agreement with proposed structure.

Other embodiments of the present invention relate to the synthesis of bisphosphonate conjugates with antibiotics, for example, aprofloxacin and/or aminoglycosidic compounds. Preparation of such conjugates will be apparent to those skilled in the art based upon the detailed description and the examples otherwise provided herein.

The bisphosphonate conjugates of the present invention are capable of releasing antibacterial and/or cytotoxic components upon binding with bone tissue, such conjugates are useful in the treatment and prevention of bone cancer, bone infections and other bone-related diseases. These bisphosphonate conjugates are also delivery vehicles for use in delivering pharmaceutical compositions to bone tissue. Methods of synthesizing of novel bisphosphonates and pharmaceutical compositions incorporating the same, and medical uses for such compositions, are provided. The novel compositions of the present invention include bone-seeking radio isotope conjugates for use in imaging and therapy.

DNA- and RNA-polymerases make two large groups of enzymes synthesizing nucleic acids. The catalyzed chemical reaction is the same for all enzymes of these groups—nucleophillic attack of 3'-OH group of the primer on P-α of the 5'-triphosphate of a ribonucleoside or deoxyribonucleoside that results in liberation of pyrophosphate. This reaction of nucleotidyl transfer is reversible-regeneration of NTPs (pyrophosphorolysis) can occur with the large concentrations of PP$_i$. In the cells pyrophosphorolysis is very low due to the large quantities of inorganic pyrophosphatase which hydrolyses pyrophosphate which in turn makes the reaction nearly irreversible. Non-hydrolysable analogs of pyrophosphate are capable of inhibition of inorganic pyrophosphatase and DNA- and RNA-polymerases. This fact can be used as a basis for the design of pyrophosphate analogs as potential therapeutics, since inhibition of nucleotide polymerizing enzymes is involved in fighting many viral infections.

The interaction of HIV-1 reverse transcriptase (HIV-RT) and DNA-dependent RNA polymerase T7 (T7-DDRP) was examined with modified nucleoside triphosphates and analogs of PP$_i$. Although T7-DDRP is not directly involved in viral diseases of higher organisms, it is a good model for transcription mechanism studies.

The following experimental results are provided for purposes of illustration and are not intended to limit the scope of the invention.

EXAMPLE 1

Synthesis of 3-amino-1-hydroxypropyliden-1,1-bisphosphonic acid

To a mixture of 12.3 g (0.15 mol) phosphoric acid, 8.9 g(0.9 mol) beta-aminopropionic acid and 50 ml chlorobenzene 33.0 g (0.24 mol) PCl$_3$ was added by dropping under stirring at 100° C. The two-layer mixture was heated at 105–110° C. for 2 h. Under those conditions the bottom layer became thick and finally became solid. The reaction mixture was cooled down to 60–65° C. At this temperature 20 ml of water was added drop by drop. The layers were stirred for 15 min., cooled down to room temperature and then they were separated. The bottom aqueous layer was filtered through paper filter. To the solution was added to 100 ml isopropanol drop by drop (60–65° C.) under stirring. The warm solution was filtered and 100 ml of ethanol was added. After 12 hours at room temperature, a precipitate was filtered off generating a yield of 12.7 g (62%) m.p. 232–234° C. To obtain a homogeneous product the solid material was boiled with 50 ml of water and insoluble substance was filtered off. Yield 10.8 g (53%), m.p. 234–236° C.

EXAMPLE 2

Synthesis of 3-(N-pyridoxylamino)-1-hydroxypropylidene-1,1-bisphosphonic acid

To the solution of 189 mg (1 mmol) 3-amino-1-hydroxypropylidene-1,1-bisphosphonic acid in water (1 ml), triethylamine (0.9 ml) and ethanol (9 ml), pyridoxal hydrochloride (408 mg, 2 mmol) was added. The reaction mixture was stirred 1 h. at room temperature. Then the pH of a solution was adjusted to 3 with 6 N HCl. Ethanol was evaporated and the pH of the solution was adjusted to 7 with NH$_4$OH. The solution was applied to a Dowex-50(H$^+$) column (20 ml). The column was washed with water and the product was eluted with 2.5% NH$_4$OH. The solution was evaporated to a small volume, the residue was dissolved in water (100 ml) and applied to a DEAE-cellulose column (HCO$_3^-$ form). The column was washed with water (200 ml) and then eluted with the use of a linear gradient NH$_4$HCO$_3$ (0.05–0.3 M). The peak eluate was evaporated and the residue coevaporated with water (5×10 ml). Lyophilization of the aqueous solution afforded the product as an ammonium salt. Yield 100 mg. 24%. R$_f$ 0.07 (B); R$_f$ 0.21 (C); R$_f$ 0.2 (D); R$_f$ 0.48 (F); R$_f$ 0,07(E).

$^1$H NMR (D$_2$O) δ: 7.55 bris, 5 (1H, 6 OH); 4.35 (2H, 5-CH$_2$); 2.45 (3H, 2-CH$_3$); 2.3 m (2H,CH$_2$)

EXAMPLE 3

Synthesis of 3-(N-[5'-phospho]pyridoxylamino)-1-hydroxypropyliden-1,1-bisphosphonic acid To the solution of 189 mg (1 mmol) 3-amino-1-hydroxypropylidene-1,1-bisphosphonic acid in water (0.5 ml), triethylamine (0.6 ml) and ethanol (2 ml), pyridoxal-5'-phosphate (265 mg, 1 mmol) was added under stirring. The reaction mixture was stirred one (1) 1 h. at room temperature, then NaBH$_4$ (38 mg, 1 mmol) was added. The solution was stirred 1 h. at room temperature. To the solution 6 N HCl (0.9 ml) was added. Ethanol was evaporated and the pH of the solution was adjusted to pH 7 with NH$_4$OH and chromatographed on DEAE-cellulose (HCO$_3$, 100 ml). The column was washed with water (200 ml) and then eluted with the use of a linear gradient NH$_4$HCO$_3$ (0.05–0.3M). The peak eluate was evaporated and the residue coevaporated with water (5×10 ml). Lyophilization of the aqueous solution afforded ammonium salt. Yield 236 mg, 44% R$_f$ 0.05 (B); R$_f$ 0.19 (C); R$_f$ 0.1(D); R$_f$ 0.03(E); R$_f$ 0.32 (F);

$^1$H NMR (D$_2$O) δ: 7.6 5 ($^1$H, 6-H); 4.3 5 (2H, 5-CH$_2$); 3.4t (2H, CH$_2$); 2.4 5 (3H, 2-CH$_3$); 2.3m (2H, CH$_2$).

$^{31}$P NMR (D$_2$O) δ: 1.75 s(1P); 17.5 s(2P)

EXAMPLE 4

Synthesis of Vitamin B6 Conjugates with aminomethylenbisphosphonate

A. Synthesis of 1-(pyridoxylamino)-methylene-1,1-bisphosphonic acid 45 mg (0.2 mmol) of ammonium salt of aminomethylenediphosphonic acid (Alferov I. S., Bobkov S. Yu., Kotlyarevsky I. L. Izvestiya AN SSSR, ser. khim., 1987, N4, 865–868) was added to a solution of 81.6 mg (0.4 mmol) of pyridoxal-HCl in 2 ml of ethanol mixed with 0.2 ml of triethylamine and 1 ml of H$_2$O. The solution was stirred at room temperature for three hours. Then 20 mg (0.5 mmol) of NaBH$_4$ was added and the reaction mixture was again stirred for three hours at room temperature. Ethanol was evaporated in vacuum, the aqueous solution was loaded on a column with Dowex-50 (H$^+$), the column was washed with water and then the product was eluted. To the aqueous solution of the corresponding acid the aqueous ammonia solution was added, then the mixture was evaporated in a vacuum to the small volume and loaded on the column with Dowex-50 (Na$^+$), the column was washed with water and Na-salt of the product was eluted and lyophilized. The yield was 62 mg, 80%.

HPLC: Nucleosil C 18 (4×250 mm); gradient 0–5 min 0% MeCN; 5–25 min 0–80% MeCN. Purity 98%; RT approximately 12 min.

TLC: R$_f$ 0.34 on PEI-cellulose in 0.5M NH$_4$HCO$_3$; R$_f$ 0.4 on silufol UV 254 in isopropanol-ammonium-H$_2$0 (3:1:2); R$_f$ 0.64 on silufol in the system isopropanol-dioxan-ammonium-H$_2$O (2:2:1:7).

$^1$H-NMR (D$_2$O) δ: 7.6 5 (1H, 6-H); 4.7 5 (2H, 4'-CH$_2$); 4.6 5 (2H, 5'-CH$_2$); 3.2 dd (1H, J$_{HP}$=16 24; N—CH); 2.45 s (3H, CH$^3$)

$^{31}$P-NMR (pH 6.3) δ: 9.2 s

B. Synthesis of 1-(N-(5'-[phospho]-pyridoxylamino)-methylene-1,1-bisphosphonic acid 57 mg (0.25 mmol) of ammonium salt of aminomethylenediphosphonic acid (Alferov I. S., Bobkov S. Yu., Kotlyarevsky I. L. Izvestiya AN SSSR, ser. khim., 1987, N4, 865–868) was added to the solution of 132.5 mg (0.5 mmol) of pyridoxal-5'-phosphate in 1 ml of H$_2$O with 0.3 ml of triethylamine. The solution was stirred at room temperature for two hours. Then 20 mg (0.5 mmol) of NaBH$_4$ was added and the reaction mixture was stirred for one hour at room temperature, then neutralized up to pH 7.0 with 2N HCl. The mixture was loaded on the column with DEAE-cellulose (HCO$_3^-$); the column was washed with water and then the product of the reaction was eluted in the gradient of NH$_4$HCO$_3$ (0.05–0.2 M). Fractions, containing the product were evaporated with water and loaded on the column with Dowex-50 (H+), the column was washed with water and then the product was eluted. To the aqueous solution of the corresponding acid aqueous ammonia solution (2.5%) was added, then the mixture was evaporated to a small volume and loaded on the column with Dowex-50 (Na$^+$), the column was washed with water and Na-salt of the product was eluted and lyophilized. The yield was 46.5 mg, 40%.

HPLC—the column Nucleosil C18, 4~50 mm. Purity—99.5%.

TLC: R$_f$ 0.08 on PEI-cellulose in 0.5M NH$_4$HCO$_3$; R$_f$ 0.2 on silufol UV 254 in isopropanol-ammonium-H$_2$0 (3:1:2).

$^1$H-NMR (D$_2$O) δ: 7.7 5 (1H, 6-H; 4.9 5 (2H, 4'-CH$_2$); 4.6 s(2H, 5'-CH$_2$); 3.3 dd (1H, J$_{HP}$=16.49; N—CH); 2.45 s (3H, CH3)

$^{31}$P NMR(D$_2$O) δ: 9.1 s (2P); 2.2 s (1P)

Figure 2:
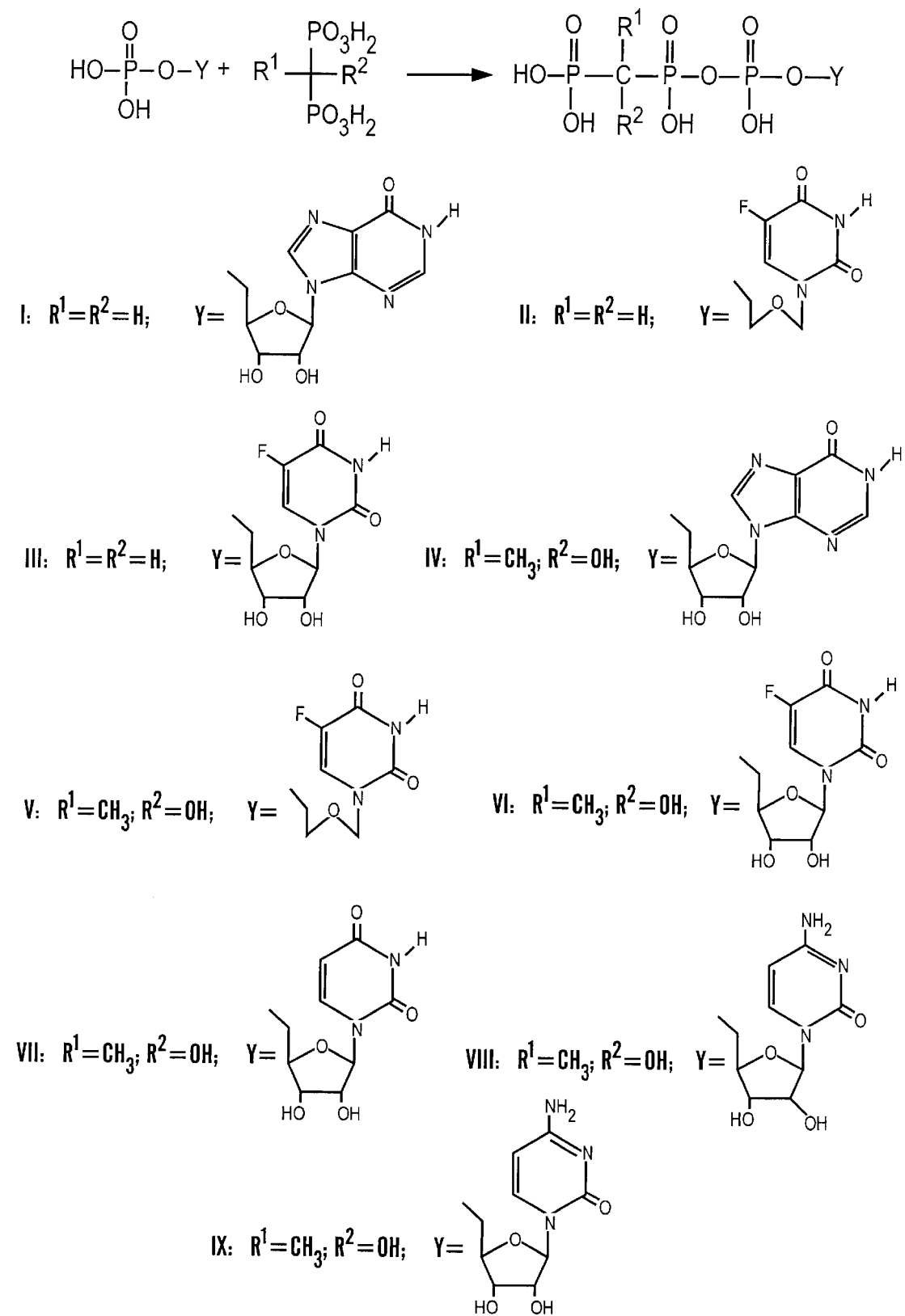
FIG. 2 is the scheme for the preparation of nucleoside 5'-triphosphate analogs.
Figure 4:
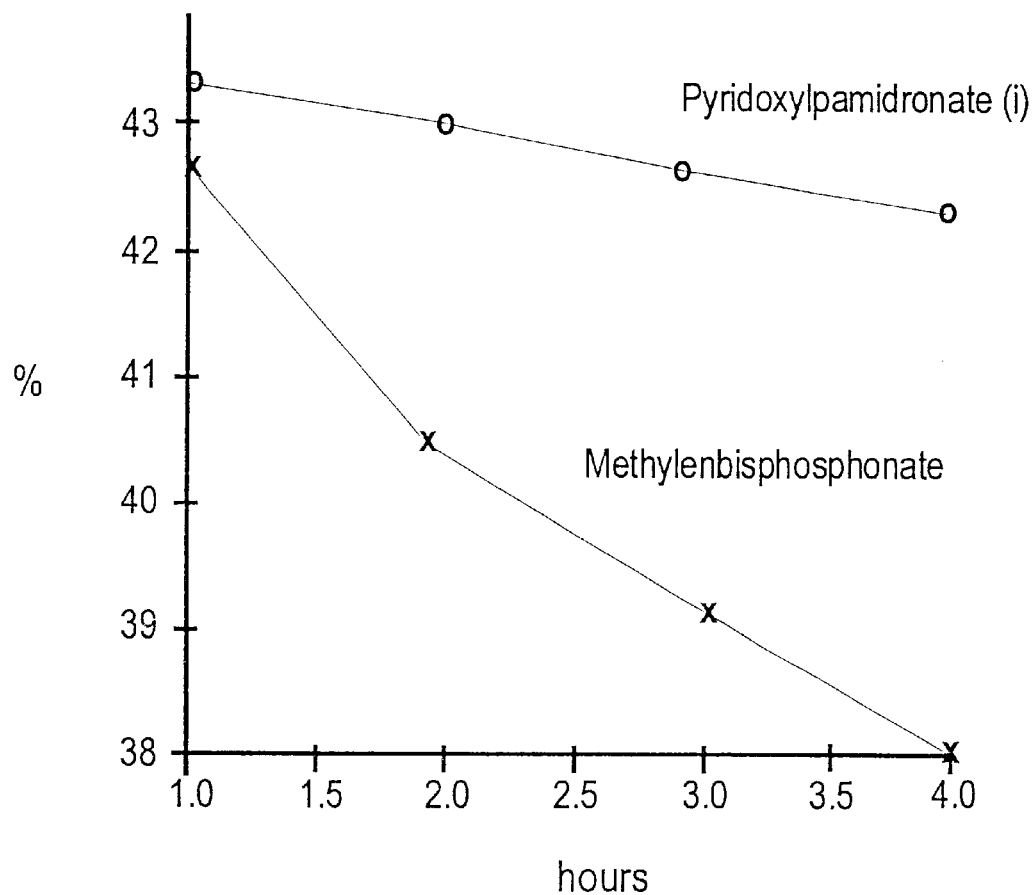
FIG. 4 shows the accumulation of radioactivity at a rat skeleton.

The synthesis of preferred bisphosphonate conjugates with nucleotides and their analogs was carried out according to FIG. 2, which is incorporated herein in its entirety.

EXAMPLE 5

Synthesis of 5-fluoro-1-(2-hydroxyethoxymethyl) uracil

The said compound was prepared according to M. Ya. Karpeisky et al, Khim. Heterocycl. Soedinenii (USSR) 1980,11, 1541–1544.

EXAMPLE 6

Synthesis of N$^4$-benzoyl-1-(2',3'-di-O-acetyl-D-arabinofuranosyl)cytosine

The compound was obtained analogously starting from N$^4$-benzoyl-D-arabinofuranosyl)cytosine (10 mmol) Yield 2.8 g (65%).

$^1$H NMR (400.13 MHz) (CDCl$_3$); 8.31 d (1H, J$_{6,5}$=7.5 Hz, H-6) 7.93–7.48 m (5H,Bz), 7.67 d (1H,H-5), 6.37 d (H1, J$_{1,2}$ 4.3 Hz, H-1'), 5.63 dd (1H, J$_{2,3}$=2.7 Hz, H-2'), 5.24 dd (1H, J$_{3',4'}$=4.1 Hz, H-3'), 4.12 ddd (1H, H4'), 4.01 dd (1H, J$_{5a,4'}$=3.6 Hz, J$_{5'a,5'b}$=12.3 Hz, H-5'a), 3.92 dd (1H, J$_{5'b,4'}$=4.7 Hz, H-5'b) 2.12×(3H, Ac), 1.98 S (3H Ac)

EXAMPLE 7

Synthesis of 5-fluorouridine 5'-monophosphate

The mixture of 2',3-di-O-acetyl-5-fluorouridine (5 mmol) and 10 ml 1M solution β-cyanoethyl phosphate in pyridine was evaporated in vacuo and dried by coevaporations with dry pyridine (2×10 ml). The residue was dissolved in 20 ml of the same solvent, N,N-dicyclohexylcarbodiimide (DCC, 40 mmol) was added and the mixture was stored at 20° C. for 4 days. After addition of water (15 ml) the precipitating dicyclohexyl urea was filtered off and washed with 50 ml of 20% aqueous pyridine. The combined filtrates were washed with ether (2×30 ml) and concentrated in vacuo to remove the traces of ether, and then applied to a column of DEAE-cellulose (200 ml, HCO$_3^-$form). The column was washed with water (500 ml) and eluted with 0.05 M solution of NH$_4$HCO$_3$. UV-absorbing fractions were combined, evaporated in vacuo, coevaporated with water (5×10 ml). The residue was dissolved in 40 ml of 1N NaOH and kept 20 min at 20° C. The solution was applied onto a column of Dowex 50 (H+form) and eluted with water, the resulting solution of monophosphate was neutralized by addition of 2.5% ammonia and evaporated in vacuo. The residue was dissolved in 50 ml of water and applied to a column of DEAE-cellulose (200 ml, HCO$_3^-$form). The column was washed with water (500 ml), 0.05 M NH$_4$HCO$_3$ and eluted with 0.1 M solution of NH$_4$HCO'$_3$. UV absorbing fractions were combined, evaporated in vacuo, coevaporated with water (5×10 ml). The residue was dissolved in 40 ml of water and freeze dried. 5-Fluorouridine 5'-monophosphate was obtained as its ammonium salt. Yield 2.4 mmol (48%).

$^1$H-NMR (400.13 MHz) (D$_2$O) δ: 8.16 d (1H, J$_{6,F}$=6.5 Hz, H-6), 5.92 dd (1H, J$_{1',2}$=4.9 Hz, J$_1$,F=1.4 Hz, H-1') 4.32 t (1H, J$_{3',2}$.=5.0 Hz, J$_{3',4}$=5.1 Hz, H-3'), 4.29 t (1H, H2') 4.22 m (1H, H4'), 4.06 ddd (1H; J$_{5'a-b}$=3.8 Hz, J$_{5'a,5b}$=11.8 Hz, J$_{5'a-p}$=2.8 Hz, H-5'a), 3.98 ddd (1H, J$_{5'b-a}$=5.1 Hz, J$_{5'b-p}$=2.9 Hz, H-5b).

EXAMPLE 8

Synthesis of 1-([2-{phosphoryloxy}ethoxy] methylene)-5-fluorouracil

The mixture of 5-fluoro-1-(2-hydroxyethoxymethyl) uracil (4.6 mmol) and 9.2 ml 1M solution of β-cyanoethyl phosphate in pyridine was evaporated in vacuo and dried by coevaporations with dry pyridine (2×10 ml). The residue was dissolved in 20 ml of the same solvent, DCC (37 mmol) was added and the mixture was stored at 20° C. for 4 days. After addition of water (15 ml), the precipitating dicyclohexyl urea was filtered off and washed with 50 ml of 20% aqueous pyridine. The combined filtrates were washed with ether (2×30 ml) and concentrated in vacuo to remove the traces of ether and then applied to a column of DEAE-cellulose (200 ml, HCO$_3^-$ form). The column was washed with water (500 ml) and eluted with 0.05 M solution of NH$_4$HCO'$_3$. Fractions absorbing in the UV were combined, evaporated in vacuo, coevaporated with water (5×10 ml). The residue was dissolved in 40 ml of 1N NaOH and kept for 20 min at 20° C. The solution was applied onto a column of Dowex 50 (H$^+$ form) and eluted with water, the resulting solution of monophosphate was neutralized by addition of 2.5% ammonia, evaporated in vacuo. The residue was dissolved in 50 ml of water and applied to a column of DEAE-cellulose (200 ml, HCO$_3^-$ form). The column was washed with water (500 ml) 0.05 M of NH$_4$HCO$_3$ and eluted with 0.1 M solution of NH$_4$HCO$_3$. Fractions absorbing in the UV were combined, evaporated in vacuo, coevaporated with water (5×10 ml). The residue was dissolved in 40 ml of water and freeze dried. 5-Fluoro-1-(2'-hydroxyethoxymethyl)uracil 2'-monophosphate was obtained as ammonium salt. Yield 2.07 mmol (45%).

$^1$H-NMR (D$_2$O) δ: 7.98 d (1H, J$_{6,F}$=5.7 Hz, H-6), 5.19 s (2H, CH$_2$N), 3.91 m (2H, CH$_2$), 3.75 m (2H, OCH$_2$)

EXAMPLE 9

Synthesis of 1-(D-Arabinofuranosyl)cytosine-5'-monophosphate

The mixture of N$^4$-benzoyl-1-(2',3'-di-O-acetyl-D-arabinofuranosyl)cytosine (2 mmol) and 4 ml 1 M solution of β-cyanoethyl phosphate in pyridine was evaporated in vacuo and dried by coevaporations with dry pyridine (2×10 ml). The residue was dissolved in 5 ml of the same solvent, DCC (16 mmol) was added and the mixture was stored at 20° C. for 4 days. After addition of water (15 ml), the precipitated dicyclohexyl urea was filtered off and washed with 50 ml of 20% aqueous pyridine. The combined filtrates were washed with ether (2×20 ml) and concentrated in vacuo to remove the traces of ether, and then applied to a column with DEAE cellulose (200 ml, HCO$_3^-$ form). The column was washed with water (500 ml) and eluted with 0.05M solution of NH$_4$HCO$_3$. Fractions absorbing in the UV were combined, evaporated in vacuo, coevaporated with water (5×10 ml). The residue was dissolved in 25 ml of 1N NaOH and kept for 20 min. at 20° C. The solution was applied onto a column with Dowex-50 (H$^+$ form) (40 ml) and eluted with a pyridine-water mixture 1:4 (100 ml). The resulting solution was evaporated in vacuo, coevaporated with water (2×10 ml) and methanol (2×20 ml). The residue was dissolved in 5 ml of 5M NH$_3$/methanol and kept at 20° C. for 4 days. The reaction mixture was dissolved in 50 ml of water, washed with chloroform (2×20 ml) and concentrated in vacuo to remove the traces of chloroform and then applied to a column of DEAE-cellulose (200 ml, HCO$_3^-$form). The column was washed with water (500 ml), 0.05 M of NH$_4$HCO$_3$ and eluted with 0.1 M solution of NH$_4$HCO$_3$. UV-absorbing fractions were combined, evaporated in vacuo, coevaporated with water (5×10 ml). The residue was dissolved in 40 ml of water and freeze dried. Yield 0.82 mmol (41%).

$^1$H NMR (400.13 MHz) (D$_2$O) δ: 7.93 d (1H, J$_{6,5}$=7.7 Hz, H-6), 6.22 d (lH', J$_{1',2}$.=5.3 Hz, H-1'), 6.08 d (1H, H-5), 4.43 t (1H, J$_{2;3}$=5.1 Hz, H-2), 4.20 t (1H, J$_{3,4}$.=5.2 Hz, H-3'), 4.15 m (1H,H-4'), 4.09 m (2H, H-5'a, 5'b)

EXAMPLE 10

Synthesis of Bisphosphonate-nucleotide Conjugates
General
NMR spectra were recorded on a Bruker AMX 400 spectrometer at 300K in D$_2$0. The chemical shifts were related to the water signal at 4.6 ppm. The signals were assigned by the aid of phosphorus decoupling measurements. The TLC-chromatography was performed on Kieselgel 60 F$_{254}$ plates developed in 2-propanol/NH$_3$(aq., conc.)/water 7:1:2 (system A); water/NH$_3$ (aq., conc.)/trichloroacetic acid/methanol 6:3:1:10 (system B) or on PI-cellulose plates in 0.25 M NH$_4$HCO$_3$ (system C); 1M LiCl (system D); 0.15 M KH$_2$PO$_4$ (system E); 0.5 M NH$_4$HCO$_3$ (system F). HPLC-analysis: Column Nucleosil C-18 (30-C18), 0–4% triethylammonium acetate (0.1M, pH6.8); 20 min flow 1 ml/min.
Protocol for Synthesis of a Conjugate
To the solution of 0.2 mmol nucleotide tri-n-butylammonium salt in DMF (3 ml) 1,1' carbonyldiimidazole (98 mg, 0.6 mmol) was added. The reaction mixture was stirred 1 h. at room temperature, than 0.8 ml 1M solution methanol in 25 ml DMF was added, after 20 min. solution of tri-n-butylammonium salt of diphosphonic acid (1 mmol) in DMF was added. The reaction mixture was stirred at room temperature 16 hours, the crystalline material was filtered off, washed with DMF, the solution was evaporated in vacuo to dryness.
Isolation and Purification
Method A (Compounds I–III, FIG. 2)
The residue after evaporating to dryness was dissolved in 20 ml water and purified on DEAE-cellulose (HCO$_3^-$). The column was washed with water (500 ml) and then eluted with the use of a linear gradient NH$_4$HCO$_3$ (0.05M–0.3M). Analogs of triphosphate were eluted in 0.21 M NH$_4$HCO$_3$. The peak eluate was evaporated, the residue coevaporated with water. Lyophilization of the aqueous solution afforded the ammonium salt of triphosphate analogs.

Method B (Compounds IV–IX, FIG. 2)

The residue after evaporating was dissolved in 20 ml of 0.02 M AcOLi in 0.02 M AcOH and chromatographed on DEAE-cellulose (AcO⁻form). The column was washed with 0.02M AcOLi in 0.02M AcOH (200 ml), 0.04M AcOLi in 0.04M AcOH (300 ml). The analog of triphosphate was eluted in 0.2M AcOLi in 0.2M AcOH. The peak eluate was evaporated, the residue was centrifuged with ethanol (4×100 ml), dissolved in water. Lyophilization of the water solution afforded the Li salt of the triphosphate analog. In the case of the analogs (VI) and (VII) residue after lyophilization was dissolved in 20 ml of 0.5% solution triethylamine in water, the solution was kept at room temperature 30 min and lyophilized. The residue was dissolved in 2 ml water and applied to a Dowex-50 (Na⁺) column. Sodium salts of triphosphate analogs were eluted with water and lyophilized.

Conjugates Obtained

Anhydride of 1-([2-{hydroxyethoxy}ethoxy]methylene)-5-fluorouracil and methylenediphosphonic acid, $NH_4$-salt, method A, (II, FIG. 2)

Yield 58 mg, 55%. $R_f$ 0.05 (A); $R_f$ 0.1(C); $R_f$ 0.32 (D); $R_f$ 0.34 (E). HPLC: 93.3%, RT 5.58 min. ($NH_4$-salt).

$^1H$ NMR ($D_2O$) δ: 7.89 d (1H, $J_{6H,F}$=5.5; 6-H); 5.25 s (2H, N—$CH_2$); 4.0 m (2H,$CH_2$); 3.78 m (2H, $CH_2$); 2.22 t (2H, J=20.0; P—$CH_2$—P).

$^{31}P$ NMR ($D_2O$) δ: −10.0 (1P, $Jp_\alpha,p_\beta$=−23.0; Pα); 11.8 m (1P, Pβ; 14.2 m (1P, Pγ).

Anhydride of 5-fluorouridine-5'-monophosphoric acid and methylenediphosphonic acid, $NH_4$-salt, method A(III, Scheme 2).

Yield 75 mg, 65%. $R_f$ 0.05 (A); $R_f$ 0.11(C); $R_f$ 0.23 (D); $R_f$ 0.4 (E). HPLC: 91.3%, RT 5.6 min.($NH_4$salt).

$^1H$ NMR($D_2O$) δ: 8.02 d (1H, $J_{6H,F}$=6.4; 6-H); 5.89 d (1H, $J_{1,2}$=3.2; 1'-H); 4.29 m (2H, 2'-H, 3'-H); 4.2m (3H, 5'-$CH_2$, 4'-H); 2.24t (2H, J=19.9; P—$Ch_2$—P).

$^{31}P$ NMR($D_2O$) δ: −10.0 d (1P, $Jp_\alpha,p_\beta$=−23.0;$P_\beta$); 11.8m (1P, $P_\beta$); 14.3 m (1P, $P_\gamma$)

Anhydride of inosine-5'-monophosphoric acid and 1-hydroxyethylidene-1,1-diphosphonic acid, Li-salt, method B, (IV, FIG. 2).

Yield 95 mg, 84%. $R_f$ 0.04 (B); $R_f$ 0.05 (C); $R_f$ 0.3 (D)); $R_f$ 0.16(E). HPLC: 99.5%; RT 8.98 min. (Li-salt).

$^1H$ NMR ($D_2O$), δ: 8.47s(1H, 8-H); 8.2 5(1H, 2-H); 6.2 br.s (1H, 1'-H); 4.6 m (2H, 2',3'-H); 4.41m (1H, 4'-H); 4.28 m (2H, 5'-$CH_2$); 1.56 t (3H, J=12,0; $CH_3$).

$^{31}P$ NMR ($D_2O$) δ: −9.3 m(1P, Pα); 17.0 m (1P, Pβ); 17.2 m (1P, Pγ).

Anhydride of 1-([2-{hydroxyethoxy}ethoxy]methylene)-5-fluorouracil and 1-hydroxyethylidene-1,1-disphosphonic acid, Li-salt, method B, (V, FIG. 2)

Yield 60 mg, 61%. $R_f$ 0.05(B); $R_f$0.09 (C); $R_f$ 0.32 (D). HPLC: 96.6%; RT 5.88 min. Na-salt).

$^1H$ NMR($D_2O$) δ: 7.72 d (1H, $J_{H,F}$=5.5; 6-H); 5.18 s (2H, N—$CH_2$); 4.09 t (2H, $CH_2$); 3.79 t (2H, $CH_2$); 1.5 t (3H, $J_{H,P}$=15; $CH_3$).

$^{31}P$ NMR ($D_2O$) δ: −8.8 d (1P, $Jp_\alpha,p_\beta$=33.3; $P_\alpha$); 16.2 dd (1P, $P_\beta$); 16.8 d (1P, $J_{P\beta,P\gamma}$=33.0; $P_\gamma$)

Anhydride of 5-fluorouridine-5'-monophosphoric acid and 1-hydroxyethylidene-1,1-disphosphonic acid Na-salt, method B, (VI, FIG. 2).

Yield 78 mg, 65%. $R_f$ 0.21 (C); $R_f$ 0.2 (D); $R_f$ 0.31 (E). HPLC: 96.6%; RT 6.18 min. Na-salt).

$^1H$ NMR ($D_2O$) δ: 7.88 d (1H, $J_{H,F}$=6.2; 6-H); 5.97 d (1H, $J_{1,2}$=4.5; 1'-H); 3.38 m (1H, 2'-H); 4.3 m (1H, 3'-H); 4.24 m (3H, 4'-H, 5'-$CH_2$); 1.54t (3H, $J_{H,P}$=14.9; $CH_3$).

$^{31}P$ NMR ($D_2O$) δ: −9.2 (1P, $J_{P\alpha P\beta}$=30.0; $P_\alpha$); 16.4 m (2P, $P_\beta$, $P_\gamma$).

Anhydride of uridine-5'-monophosphoric acid and 1-hydroxyethylidene-1,1-diphosphonic acid, Li-salt, method B (VII, FIG. 2).

Yield 80 mg, 75%. $R_f$ 0.1 (C); $R_f$ 0.12 (D); $R_f$ 0.04 (E). HPLC:97.3%; RT 3.49 min., Na-salt).

$^1H$ NMR ($D_2O$) δ: 7.8d (1H, $J_{6,5}$ 7.8; 6-H); 5.9 d (1H, $J_{1',2'}$=3.8; 1'-H); 5.8 dd (1H, $J_{5,6}$=7.8; 5-H); 4.3m (1H, 2'-H); 4.2m (1H, 3'H); 4.19 m (3H, 4'-H, 5'-$CH_2$); 1.45t (3H, $J_{P,H}$=15.0; $CH_3$).

$^{31}P$ NMR ($D_2O$, pH 9.3) δ: −9.2d (1P, $J_{P\alpha P\beta}$=32.0; $P_\alpha$); 16.2m (2P, $P_\beta$, $P_\gamma$); ($D_2O$ pH5.3) δ: −9.2d (1P, $J_{P\alpha P\beta}$=31.7; Pα); 2.8 dd (1P, $J_{P\beta,P\gamma}$=33.7, Pβ;) 17.8 d (1P, $J_{P\gamma,P\beta}$=33.7; $P_\gamma$)

EXAMPLE 11

Synthesis of Anhydride of inosine-5'-monophosphoric Acid and methylenedisphosphonic Acid, $NH_4^+$ Salt, (I, FIG. 2)

To the solution of 0.2 mmol Inosine-5'-monophosphate tri-n-butylammonium salt in dry DMF (3 ml) 1,1'-carbonyldiimidazole (98 mg, 0.6 mmol) was added. The reaction mixture was stirred 1 h at room temperature. TLC analysis in system iso-PrOH—$NH_4OH$—$H_2O$ (7:1:2) showed that mononucleotide was completely converted to a imidazolide (Rf 0.1->0.6). The 0.8 ml 1M solution methanol in dry DMF was added, after 20 mm solution of tri-n-butylammonium salt of methylenediphosphonic acid (1 mmol) in DMF (3 ml) was added. The reaction mixture was stirred 16 h. at room temperature. The crystalline material was filtered off, washed with DMF and the solution was evaporated in vacuo to dryness. The residue, after evaporating, was dissolved in 20 ml water and was applied on to column of DEAE-cellulose (100 mI, $HCO_3^-$form). The column was washed with water (500 mI) and then eluted with the use of linear gradient of $NH_4HCO_3$ (0.05->0.3 M). The triphosphate analog was eluted in 0.21 M $NH_4HCO_3$. The peak eluate was evaporated and the residue was coevaporated with water (5×10 ml). Lyophilization of the water solution afforded ammonium salt of triphosphate analog. Yield 85 mg, 74%. $R_f$: 0.05 (A); 0.04 (B);0.25(C); 0.16 (D). HPLC (Column Nucleosil C-18 (30-C18), 0–4% triethylammonium acetate (0.1M, pH 6.8), 20 min. flow rate 1 mL/min): 100%, RT 7.2 min, Na salt)

$^1H$ NMR ($D_2O$) δ: 8.45 s (1H, 8-H); 8.2 s (1H, 2-H); 6.1 d (1H, $J_{1,2}$=5.4; 1'-H); 4.55 m (1H, 3'-H); 4.39 m (1H, 4'-H); 4.25 m (2H, 5'-$CH_2$); 2.32 t (2H, $J_{H,P}$=20; P—$CH_2$—P).

$^{31}P$ NMR ($D_2O$) δ: −10.2 d (1P, $J_{P\alpha P\beta}$=25; $P_d$); 9.8 br d (1P, $P_\beta$); 15.4 d (1P, $J_{P\beta,P\gamma}$=7.0; $P_\gamma$)

EXAMPLE 12

Synthesis of Anhydride of 1-(2-phosphonooxyethoxymethylene-5-fluorouracil and 1-hydroxyethyliden-1,1-diphosphonic Acid, Li Salt (V, FIG. 2).

To the solution of 0.2 mmol 1-(2-hydroxyethoxymethylene)-5-Fluorouracil-2'-phosphonic acid tri-n-butylammonium salt in dry DMF (3 ml) 1,1'-carbonyldiimidazole (98 mg, 0.6 mmol) was added. The reaction mixture was stirred 1 h. at room temperature. TLC analysis in system iso-PrOH—$NH_4OH$—$H_2O$(7:1:2) showed that mononucleotide was completely converted to an imidazolide ($R_f$ 0.15->0.65). Then 0.8 ml 1M solution methanol in dry DMF was added, after 20 min solution of tri-n-butylammonium salt of 1-hydroxyethylidene-1,1- diphosphonic acid (1 mmol) in DMF (3 ml) was added. The reaction mixture was stirred 16 h. at room temperature. The crystalline material was filtered off and washed with DMF. The solution was evaporated in vacuo to dryness. The residue, after evaporating, was dissolved in 20 ml 0.02M AcOLi in 0.02M AcOH and was applied on to column of DEAE-cellulose (100 ml, AcO-form). The column was washed with 0.02 N AcOLi in 0.02M AcOH(200 ml), 0.04M AcOLi in 0.04M AcOH (300 ml). The triphosphate analog was eluted in 0.2M AcOLi in 0.2M AcOH. The peak eluate was evaporated, the residue was centriftiged with ethanol (4×100 ml) and was then dissolved in water. Lyophilization of the water solution afforded Li salt of triphosphate analog. Yield 60 mg, 61%. Rf; 0.05 (B); 0.09 (C); 0.32 (1)). HPLC (Column Nucleosil C-18 (30-C 18), 0–4% triethyl ammonium acetate (0.1 M, pH 6.8), 20 mm, v.1 ml/min): 96.6%, RT 5.88 min (Na salt)

$^1$H NMR (D$_2$O) δ: 7.72 d (J$_{H-F}$=5.5; 6H); 5.18 s (2H, N-5 CR$_2$); 3.79 t (2H, CH$_2$); 1.5 t (3H, J$_{H,P}$=15; CH$_3$)

$^{31}$P NMR (D$_2$O) δ: -8.8 d (1P, J$_{P\alpha P\beta}$=33.3; Pα;); 16.2 dd (1P, 1P, J$_{P\beta,P\gamma}$=7.0; Pγ)

EXAMPLE 13

Synthesis of Anhydride of 5-fluoro-uridine-5'-monophosphoric Acid and 1-hydroxyethylidene-1,1-diphosphonic Acid, Li Salt (VI, Scheme 2).

To the solution of 0.2 mmol 5-Fluoro-uridine-5'-monophosphate tri-n-butylammonium salt in dry DMF (3 ml) 1,1'-carbonyldiimidazole (98 mg, 0.6 mmol) was added. The reaction mixture was stirred 1 h. at room temperature. TLC analysis in system iso-PrOH—NH$_4$OH—H$_2$O (7:1:2) showed that mononucleotide was completely converted to a corresponding imidazolide (R$_f$ 0.13->0.7). Then 0.8 ml 1M solution methanol in dry DMF was added, after 20 min solution of tri-n-butylammonium salt of 1-hydroxyethylidene-1,1-diphosphonic acid (1 mmol) in DMF (3 ml) was added. The reaction mixture was stirred 16 h. at room temperature. The crystalline material was filtred off, washed with DMF, and the solution was evaporated in vacuo to dryness. The residue, after evaporating, was dissolved in 20 ml 0.02M AcOLi in 0.02M AcOH and was applied on to column of DEAE-cellulose (100 ml, AcO$^-$-form). The column was washed with 0.02 M AcOLi in 0.02 M AcOH (200 ml), 0.04 M AcOLi in 0.04 M AcOH (300 ml). The triphosphate analog was eluted in 0.2 M AcOLi in 0.2M AcOH. The peak eluate was evaporated, the residue was centrifuged with ethanol (4×100 ml), dissolved in 15 ml water and freeze dried. The residue was dissolved in 20 ml of 0.5% solution of triethylamine in water and kept for 30 min. at 20° C. and freeze dried. The residue was dissolved in 2 ml water and was applied on to a column of Dowex-50 (1 ml, Na$^+$-form). The Na salt of triphosphate analog was eluted with water and freeze dried. Yield 78 mg, 65%. R$_f$: 0.05 (B); 0.21 (C); 0.2 (D); 0.31(E). HPLC (Column Nucleosil C-18 (30-C18), 0–4% triethylammonium acetate (0.1 M, pH 6.8), 20 min., flow rate 1 ml/min): 96.6%, RT 6.18 min (Na salt)

$^1$H NMR (D$_2$O) δ: 7.88 d (1H, J$_{H,F}$=6.2; 6-H); 5.97 d (1H, J$_{1',2'}$4.5; 1'-H); 3.38 m (1H, 2'-H); 4.3 m (1H, 3'-H); 4.24 m (3H, 4'-H, 5'-CH$_2$); 1.54 t (3H, J$_{H,P}$=14.9; CH$_3$).

EXAMPLE 14

Stability of Novel Bisphosphonate Conjugates

A. Determination of a Conjugate-Technetium Complex Stability

The stability of complexes formed under different conditions (water, human plasma and serum) was estimated by chromatography methods. Chromatographic studies were carried out using acetonitrile-water (3:1) solvent system. Whatman 3M paper strips (8 cm×2 cm) were used for ascending chromatography. Strips were cut into 0.5 cm sections and assayed for radioactivity, and the percent binding was determined for the labeled conjugate. Pertechnetate R$_f$ value were equal to 1.0 under these conditions. The radioisotope complex was incubated in water (24 hours), fresh human plasma and serum (5 hours) at 37° C. Samples were then withdrawn from the stirred plasma or serum immediately (at time zero) after addition and then each hour. The main product (more than 97%) was represented by compound with R$_f$=0.1 in all experiments.

TABLE 1

Chromatographic estimation of $^{99m}$Tc-pyridoxyl-pamidronate(i) complex stability in aqueous solution at pH 7.0

| R$_f$\Time | 0 | 1 hour | 5 hours | 24 hours |
|---|---|---|---|---|
| 0.1 | 98.7 | 98.5 | 98.9 | 88.48 |
| 0.2 | 0.1 | 0.25 | 0.16 | 8.52 |
| 0.3 | 0.1 | 0.12 | 0.20 | 0.53 |
| 0.4 | 0.07 | 0.08 | 0.10 | 0 |
| 0.5 | 0.11 | 0.10 | 0.07 | 0.14 |
| 0.6 | 0.12 | 0.15 | 0.09 | 0.41 |
| 0.7 | 0.16 | 0.11 | 0.05 | 0.15 |
| 0.8 | 0.18 | 0.08 | 0.13 | 0 |
| 0.9 | 0.14 | 0.08 | 0.08 | 1.33 |
| 1.0 | 0.33 | 0.49 | 0.26 | 0.55 |

\* The complex was prepared according to standard protocol
\*\* Figures in Table represent distribution of radioactivity on chromatogram as % of initial radioactivity of the probe taken at time zero.

B. Stability of Nucleotide-bisphosphonate Conjugates

Figure 3:
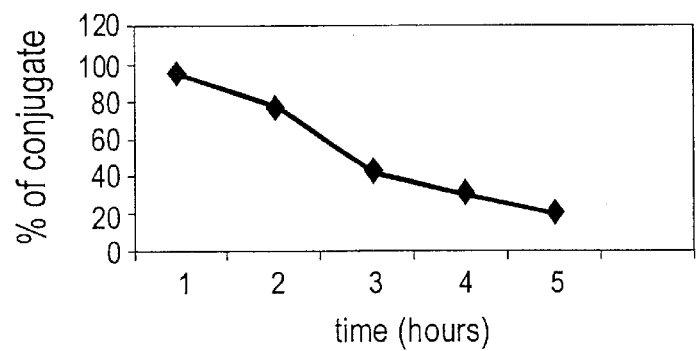
FIG. 3 demonstrates the stability of (HO)2P(O)—C(—OH)(—CH$_3$)—P(O)(OH)—O—P(O)(OH)-5-F-Urd (conjugate VI) in human serum.

HPLC-analysis of hydrolytic stability of conjugate VI, FIG. 2, in buffer and in human serum was carried out under the following conditions: column Nucleosil C-18 (30-C18), 0–4% triethylammonium acetate (0.1 M, pH6.8); 20 min, flow rate –1 ml/min. The conjugate VI was found to be stable for several hours (more than 97%) in buffer solution at pH 5–7. Hydrolytic cleavage of the conjugate P—O—P bond occurred in course of incubation either at pH>8.0 or at pH<3.0. The stability of the conjugate was decreased in mouse/human serum as it is evidenced from data on FIG. 3. However, the conjugate is stable enough to be delivered to a skeleton in intact form.

EXAMPLE 15

Binding of Novel Bisphosphonate Conjugates (NBC) on Hydroxyapatite Powder

To estimate the binding of NBC on hydroxyapatite (the mineral component of bone) UV spectra of NBC at pH7 were recorded before and after treatment with hydroxyapatite. The suspension of hydroxyapatite in water (10 ml) was added to 1 ml of ~10$^{-4}$ M solution of a NBC in 0.1 M Tris-HCl buffer, (pH 7.0), containing 0.15 M NaCl and the mixture was intensively shaken for 10 minutes, and then centrifuged for 5 minutes at 10000 rpm. The supernatant was separated and an absorption spectrum of the supernatant was recorded. The corresponding values of peaks absorbency before and after hydroxyapatite treatment are given in Table 2.

TABLE 2

UV-spectra of novel bisphosphonate conjugates

| Compound | wavelength of peaks, nm | Before hydroxyapatite addition | After hydroxyapatite addition | % of nonbound compound | % of bound compound |
|---|---|---|---|---|---|
| I* | 249 | 1.158 | 0.086 | 7.43 | 92.57 |
| II* | 266 | 0.667 | 0.085 | 12.74 | 87.26 |
| III* | 269 | 0.778 | 0.233 | 29.95 | 70.05 |
| VI* | 269 | 0.567 | 0.172 | 30.34 | 69.66 |
| VIII* | 272 | 0.795 | 0.09 | 1 1.32 | 88.68 |
| (i)** | 326 | 0.391 | 0 | 0 | 100 |
| (ii)** | 326 | 0.758 | 0 | 0 | 100 |
| (iii)** | 326 | 0.462 | 0 | 0 | 100 |
| (iv)** | 326 | 0.463 | 0 | 0 | 100 |

*Nucleoside triphosphate analogs (numbering as on Scheme 2)
**Vitamin B6 -bisphosphonate conjugates;
(i) 3-(N-[5'-phospho]-pyridoxylamino)-hydroxypropylidene 1,1-bisphosphonic acid
(ii) 3-(N-pyridoxylamino)-1-hydroxypropylidene), 1,1-bisphosphonic acid
(iii) 1-(N-[5'-phospho]-pyridoxylamino)-methylene-1,1-bisphosphonic acid
(iv) 1-(N-pyridoxylamino)-methylene-1,1-bisphosphonic acid

EXAMPLE 16

Biodistriblitions in Rats of Vitamin B6-bisphosphonate Conjugates in Complex with $^{99m}Tc$ Preparation of the Composition for a Diagnostic Test The probes were prepared with molar concentration of about $10^{-3}$ molar at pH 6.5, with a molar ratio $SnCl_2$ to a conjugate 1:10 and 1 $m^{ci}$/ml pertechnetate.

Determination of Biodistributions in Rats

Male rats weighting 160–140 g were injected intravenously via the tail vein. The rats were sacrificed and dissected at selected times—30 min., 60 min., and 120 min. The activity uptake in bone, blood, muscle, liver and spleen of each rat was measured. The results obtained indicate 40–45% of initial radioactivity injected was accumulated at bone skeleton after 60–90 min.

TABLE 3

Ratio (%) of radioactivity accumulated in bone to that of other organ/tissue

| | Bone/muscle 0 min; 60 min; 120 min | Bone/blood 0 min; 60 min; 120 min | Bone/liver + spleen 0 min; 60 min; 120 min |
|---|---|---|---|
| Medronate | 5.1; 42.2; >80 | 20.1; 47.5; >380 | 6.0; 63.3; 112.3 |
| Formulation 1 | 6.4; 94.8; >80 | 12.2; 316; 456.4 | 54.7; 220.0; 313.7 |
| Formulation 2 | 8.7 24.2; >80 | 16.4; 43.4; 216.7 | 6.5; 132.4; 247.6. |

*Medronate-commercially available standard preparation on basis of methylenbisphosphonate
**Formulation 1-preparation on basis of 3-(pyridoxylamino)-1-hydroxypropylidene-1,1-bisphosphonic acid
Formulation 2-preparation on basis of 3-(5'-phosphopyridoxylamino)-1-hydroxypropylidene-1,1-bisphosphonic acid
***Each figure represents average from 3 rats

EXAMPLE 17

Application of Compositions of Vitamin B6-bisphosphonate Conjugates for Bone Imaging Once the complex was determined to be stable in PBS and fresh plasma, a series of gamma camera imaging studies were performed wherein imaging results are determined at time points beyond two hours, and preferably at 4 and at 6 hours. The blood pool utilized should preferably be cleared by time points beyond two hours and the bony skeleton should be obvious as in bone images using Medronate-$^{99m}Tc$ images.

Two rabbits were used for experiments to compare radioactivity accumulation on normal and damaged leg. A periostium (2×0.5 cm) was removed from one of a rabbit's leg and pyridoxylpamidronate (i) preparation (1.2 ml; 5 mCi) was injected into vein after 14 days (time needed for bone's callosity to form). Radioactivity accumulation in a damaged area was checked after 3 hours. Results expressed in number of impulses are given in Table 4.

TABLE 4

Accumulation of radioactivity at rabbit leg

| Organ/Rabbit | Rabbit 1 | Rabbit 2 |
|---|---|---|
| Damaged leg | 3408 | 5124 |
| Normal leg | 2048 | 3362 |
| Ratio | 1.66 | 1.52 |

The main aspect of the present invention relates to novel bisphosphonate conjugates that are capable of delivering antibacterial and/or anti-neoplastic (cytotoxic) residue to the bone and surrounding tissues. Such conjugates will release their therapeutic component upon binding to the bone tissue and thus are useful in the treatment and prevention of bone primary tumor, bone metastases and bone infections.

To find substances that are useful for the treatment of the primary bone tumors, as well as bone metastasis, the present inventors designed, synthesized and tested novel bisphosphonate conjugates containing both an osteotropic and an antineoplastic (cytotoxic) moiety released upon binding of said conjugates to bone. The chemical covalent bond(s) connecting bisphosphonate residue and a drug is both stable enough to survive in the bloodstream and yet is cleaved to liberate drug when the conjugate binds to bone.

For example, in the case of osteomyelitis (bone infection), certain therapeutic antibiotics can be coupled to the bisphosphonate carrier molecule for delivery of high concentrations of antibiotic to sites of bone infection. Examples of antibiotics include ciprofloxacin (a fluoroquinolone), ampicillin (a penicillin antibiotic), gentamycen (an aminoglycoside antibiotic) and cefalex (a cephalosporin antibiotic). The present invention thus provides certain novel bisphosphonate conjugates, pharmaceutical compositions, and methods of using such analogs in the treatment of bone cancer and other bone-related diseases. Examples of the anti-cancer compounds include but are not limited to nucleoside and deoxynucleoside derivatives such as 5-fluroouridine, 5-fluoro-2'-deoxyuridine and cytarabine, as well as inosine derivatives. The biological activity of such conjugates is demonstrated using appropriate in vitro and in vivo models. The pharmaceutically acceptable salts and esters of the invention are characterized in that they have the general structures:

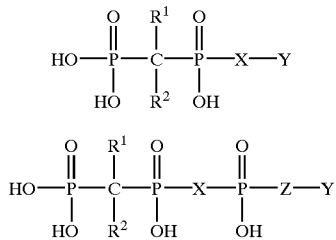

where X can be O, S or N; Z can be O, S, N; Y=residue of anti-cancer or antibiotic compound.

R1=H;

R2=R3, OR3, NR3, SR3

R3=H, alkyl, aryl, cycloalkyl, heteroaryl, NH2.

They thus comprise (A) esters, thioesters or amides of substituted methylenebisphosphonate, and (B) anhydrides formed between a substituted methylenebisphosphonate and a phosphate, thiophosphate or phosphoramidate, which can be considered as analogs of triphosphates. Phosphoanhydride bonds in such analogs are labile enough to provide release of the therapeutic compound upon binding with the bone or surrounding tissues.

One aspect of the present invention is thus directed to the synthesis of pharmaceutical compositions and medical uses of such compositions. Particular embodiments of the present invention include anti-cancer drugs that are coupled to substituted methylenebisphosphonate, such drugs including but not limited to nucleoside and deoxynucleoside derivatives, cytarabine, cisplatin, doxorubicin, methotrexate, antisense- and catalytic oligonucleotides, antibiotics such as ciprofloxacine, aminoglycosides, penicillin, cephalosporins, quinolones, protein toxins and protein or peptide growth factors or hormones that promote bone growth and bone marrow proliferation. Yet a further aspect of the present invention relates to the synthesis of novel bisphosphonates, pharmaceutical compositions incorporating the same and medical uses for such compositions.

While various embodiments of the present invention have been described in detail, it will be apparent that further modifications and adaptations of the invention will occur to those skilled in the art. It is to be expressly understood that such modifications and adaptations are within the spirit and scope of the present invention.

What is claimed is:

1. A composition for targeting bone and bone-surrounding soft tissue comprising:

a) a B6-bisphosphonate conjugate having the structure:

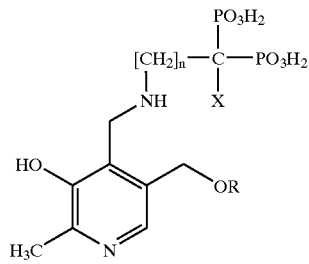

or a pharmaceutically acceptable salt thereof, wherein n=0–6;

R=H, $PO_3H_2$, $SO_3H$;

X=H, OH, $NH_2$, $SR^2$, alkyl, aryl or heteroaryl; and, $R^2$=H, alkyl, aryl, or heteroaryl, b) a therepeutical or imaging radionuclide, and c) a reducing agent.

2. The composition of claim 1, wherein the radionuclide is selected from the group consisting of pertechnetate and rhenate.

3. The composition of claim 2, wherein the radionuclide is selected from the group consisting of technetium-99m, rhenium 184 and rhenium 186.

4. The composition of claim 1, wherein the reducing agent is selected from the group consisting of tin, iron and chromium.

5. The composition of claim 1, wherein the reducing agent is a stannous salt.

6. The composition of claim 1, additionally comprising a stabilizer.

7. The composition of claim 6, wherein the stabilizer is selected from the group consisting of ethanol, nitrate, nitrite and para-aminobenzoic acid.

8. The composition of claim 1, additionally comprising an inert dispersing agent.

9. The composition of claim 1, wherein the B6-bisphosphonate conjugate is 3-(N-pyridoxylamino)-1-hydroxypropyliden-1,1-bisphosphonic acid.

10. A composition for targeting bone and bone-surrounding soft tissue comprising 3-(N-pyridoxylamino)-1-hydroxypropyliden-1,1-bisphosphonic acid, a radionuclide selected from the group consisting of technetium-99m, rhenium 184 and rhenium 186, a reducing agent selected from the group consisting of tin, iron and chromium, and a stabilizer selected from the group consisting of ethanol, nitrate, nitrite and para-aminobenzoic acid.

11. A method of performing a bone scan comprising:

administering to an individual a bone scanning-effective amount of a composition of claim 1; and, scanning the individual to produce a bone image.

* * * * *